US008202689B2

(12) United States Patent
Heller et al.

(10) Patent No.: US 8,202,689 B2
(45) Date of Patent: Jun. 19, 2012

(54) NANOFABRICATION PROCESSES AND DEVICES FOR THE CONTROLLED ASSEMBLY OF FUNCTIONALIZED NANOSTRUCTURES

(75) Inventors: Michael Heller, San Diego, CA (US); Benjamin Sullivan, San Diego, CA (US); Dietrich Dehlinger, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 1052 days.

(21) Appl. No.: 11/914,122

(22) PCT Filed: May 11, 2006

(86) PCT No.: PCT/US2006/018611
§ 371 (c)(1),
(2), (4) Date: Jun. 2, 2008

(87) PCT Pub. No.: WO2006/122317
PCT Pub. Date: Nov. 16, 2006

(65) Prior Publication Data
US 2009/0221443 A1        Sep. 3, 2009

Related U.S. Application Data

(60) Provisional application No. 60/679,954, filed on May 11, 2005.

(51) Int. Cl.
*C12Q 1/68* (2006.01)
(52) U.S. Cl. .......................................................... 435/6.1
(58) Field of Classification Search .................... 435/6.1
See application file for complete search history.

(56) References Cited

U.S. PATENT DOCUMENTS 6,780,584 B1 *   8/2004   Edman et al. ................. 435/6.19
2003/0215376 A1 *  11/2003   Chopra .......................... 422/942

OTHER PUBLICATIONS

Fu et al. "Discrete Nanostructures of Quantum Dots/AU with DNA" J. Am. Chem. Soc. (Aug. 2004) vol. 126, pp. 10832-10833.*

* cited by examiner

*Primary Examiner* — Jerry Lin
(74) *Attorney, Agent, or Firm* — AlbertDhand LLP

(57) ABSTRACT

The invention relates to processes and devices for the controlled fabrication of nanostructures from starting components that have high fidelity recognition properties and multiple binding groups. In one embodiment, the invention relates to the formation of nanostructures using controlled sequential addition of nanocomponents at regular intervals via sequential formation of binding pairs or other chemical binding reactions.

30 Claims, 7 Drawing Sheets

NANOFABRICATION PROCESSES AND DEVICES FOR THE CONTROLLED ASSEMBLY OF FUNCTIONALIZED NANOSTRUCTURES

TECHNICAL FIELD

The invention relates to processes and devices for the controlled fabrication of nanostructures from starting components that have high fidelity recognition properties and multiple binding groups. In one embodiment, the invention relates to the formation of nanostructures using controlled sequential addition of nanocomponents at regular intervals via sequential formation of binding pairs or other chemical binding reactions.

BACKGROUND OF THE INVENTION

Presently, without the use of complex chemical blocking group procedures, it is very difficult to control the assembly of molecules and nanocomponents that have high fidelity recognition properties and multiple binding groups into higher order nanostructures. By way of example, it is difficult to maintain the self-assembling properties of a multiply derivatized or functionalized molecule such as a biotinylated DNA sequence, when attempting to further react that biotinylated DNA molecule with a multiply functionalized nanoparticle (such as streptavidin derivatized quantum dots). The direct mixing of a multiply biotinylated DNA sequence with streptavidin-nanoparticles leads to considerable non-specific intermolecular and intramolecular strand crosslinking of the biotinylated DNA with nanoparticles. Even under the most stringent conditions of controlled stoichiometric mixing of biotinylated DNA with the streptavidin nanoparticles, only a few transient viable structures are produced which then quickly crosslink into useless aggregates. Thus, even though high fidelity recognition sequences still exist in the DNA and biotin/streptavidin binding sites are still present, the ability to use those properties for any further viable self-assembly or binding is gone.

There have been a few recent reports of the use of electrophoretic nanopore structures or complex gel permeation to identify and synthesize biomolecules. For example, see U.S. Pat. No. 6,780,584 which describes an electronic system for performing molecular binding reactions. In addition, methods for making nanopore structures are known, such as the method for manufacturing nanopore systems described in U.S. Published application 2003/0215376 which is reported to be useful for identification and characterization of biomolecules. However, the use of nanopore structures as a molecular barrier in performing biomimetic synthesis of higher order nanostructures has not yet been described.

Accordingly, the present invention represents a combination of bottom-up processes with top-down processes that allow the creation of higher order heterogeneous and hybrid two and three dimensional nanostructures.

SUMMARY OF THE INVENTION

Most broadly, this invention relates to devices, techniques and methodologies which allow for the controlled synthesis, assembly, organization, or fabrication of unique complex higher order two and three dimensional macromolecular structures, microstructures and macroscopic sized structures from starting components that have high fidelity recognition and multiple chemically reactive or ligand binding groups. The key to such systems and methods is the formation of "nanostructures" as described herein.

Starting components include, but are not limited to: multiply functionalized-high fidelity recognition biopolymers such as DNA, RNA and polypeptides; organic polymers and inorganic polymers; biomolecules such as proteins, enzymes and antibodies; macromolecules such as dendrimers, fullerenes, cyclodextrans, crown ethers, micelles and vesicles; nanoparticles and nanomaterials such as quantum dots; and metallic nanoparticles, semiconductor nanoparticles, polymeric nanoparticles, carbon nanotubes and other nanotube, nanorod and nanowire structures.

Functional moieties include, but are not limited to, components that contain chemically reactive groups such as amines, carboxyl, aldehyde, sulfhydral groups or combinations of such chemically reactive groups; and to components that contain ligand binding groups such as biotin/streptavidin, antibody/antigen, metal chelating or coordination structures, or combinations of those binding groups. Components which contain combinations of both chemical binding and ligand binding groups are also anticipated by the invention. The process of this invention involves placing different multiply functionalized components (multiple reactive/binding groups) into separate fluidic chambers separated by a defined nanopore membrane structure (i.e., a "nanopore structure".) A nanopore structure can be a membrane or other type of barrier with a controlled pore size, pore shape, pore spacing and/or pore length (collectively referred to herein as "pore morphology".) The nanopores can also be modified to enhance or improve their transport and/or selective properties.

By way of example, the practice of the present invention may involve a first group of multiply functionalized components in one chamber that are actively transported through the pores in the nanopore structure into the second chamber containing a second group of multiply functionalized components. "Active transport" refers to facilitating the movement through the nanopores via the application of a driving force, and includes but is not limited to: electrophoretic and/or electroosmotic transport, pumping, pressure, centrifugation, or other ways of applying forces to selectively "move" molecular components that are known in the art. The controlled emergence of the first multiply functionalized components into the second chamber containing the second multiply functionalized components allows the two components to selectively react or bind in a predictable sequential fashion favoring assembly into the desired viable higher order nanostructure. The competing nonspecific intermolecular and intramolecular cross linking reactions are greatly minimized or eliminated by the process.

In one embodiment, this invention relates to a controlled bottom-up nanofabrication assembly process utilizing electric fields and a chambered nanopore device with an arrangement of compartments (i.e., two or more "chambers") separated by one or more nanopore structures. The process and nanopore device can be used to control the self-assembly, organization, specific modification, synthesis, and fabrication of higher order nanostructures from high fidelity recognition multiply functionalized biopolymer components with multiply functionalized nanoparticle components.

The high fidelity recognition multiply functionalized biopolymer molecules (i.e., "derivatized polymers") in one chamber can include, but are not limited to multiply functionalized DNA, RNA, PNA (peptide nucleic acids) oligonucleotides, polypeptides, or other self-assembling linear biomolecules. Such derivatized polymers are functionalized at "regular intervals", which means that they are assembled and functionalized (either before, during or after assembly) at locations along the polymer backbone that are predetermined. As such, functional groups may be spaced apart evenly or unevenly or to coincide with a predetermined probability of functionalization.

The multiply functionalized nanocomponents in another chamber can include but are not limited to functionalized quantum dots, metallic nanoparticles, polymeric nanoparticles, and nanotube structures.

Using the chambered nanopore device of the invention, high fidelity recognition multiply functionalized biopolymer molecules can thus be reacted in a controlled sequential fashion with multiply functionalized nanocomponents to form the precursor of a viable higher order nanostructure. More particularly, using the intrinsic high fidelity recognition properties of the first order nanostructures created by the device, the nanostructures may now be further self-assembled into even larger two or three dimensional structures, materials and devices with microscopic or macroscopic dimensions (i.e., "higher order nanostructures".)

By way of another example, the invention teaches how multiply functionalized DNA components and multiply functionalized nanocomponents such as quantum dots can be assembled using a nanopore structure, which is part of the chambered nanopore device, so as to produce high molecular weight linear DNA constructs with multiply functionalized nanocomponents attached at precise locations along the DNA backbone structure (i.e. at "regular intervals".) Starting components such as multiply biotinylated DNA molecules and streptavidin derivatized quantum dots are held in separate fluidic chambers separated by the nanopore structure. The multiply biotinylated DNA molecules in the first chamber are transported (e.g., electrophoretically) through the pores in the nanopore structure into the second chamber containing the streptavidin-quantum dots. The controlled emergence of the multiply biotinylated DNA sequences into the second chamber containing the streptavidin-quantum dots allows the two components to bind (via the assembly of binding pairs or via chemical reaction) in a predictable sequential fashion favoring assembly of the desired nanostructure, such as the linear DNA-quantum dot nanostructures as depicted in FIGS. 1-3. The competing nonspecific intermolecular and intramolecular cross linking reactions are greatly minimized or eliminated by the process (see FIG. 4.) The linear DNA-quantum dot structures from the process can now be further derivatized by reaction of the remaining streptavidin functional groups (on the quantum dots) with an appropriate biotinylated moiety to sheath the DNA-quantum dot structure (see FIG. 5.)

Other related aspects of the invention include the use of the primary electric field nanopore process to assemble individual sets of linear double-stranded DNA/nanocomponent structures, each of which have a different type of nanocomponent attached to the DNA. Such DNA strands can then specifically cleaved into individual segments containing one type of nanocomponent. A complementary template DNA strand can be designed and synthesized to which any given combination of the different DNA/nanocomponent segments can be hybridized. See FIG. 6. This unique secondary process allows the creation of any desired linear combination of nanocomponents onto a template DNA sequence.

Another aspect of the invention relates to the use of a combined electrophoretic/electroosmotic nanopore process which allows linear mono- and di-derivatized DNA/nanocomponent constructs to be separated from starting nanocomponents and nonlinear constructs. Overall, the devices and processes of this invention overcome several fundamental problems in self-assembly based nanofabrication: first, how to carry out the controlled sequential assembly or further modification of multiply functionalized highly reactive molecular and nanoscale components into higher order structures; second, how to eliminate or greatly reduce competing non-specific intermolecular and intramolecular cross linking reactions; and third, how to maintain the further self-assembly, organizational and high fidelity recognition properties of nanostructures throughout the process.

The sheathing of the linear DNA-quantum dot nanostructure depicted in FIG. 5 can be used to reduce quenching, and to improve the photonic transfer efficiency, robustness and other performance properties of the nanostructures. Subsequently, the high fidelity base pairing recognition properties within the DNA-quantum dot nanostructure can be used for further self-assembly (via hybridization) into higher order interconnected structures. Such linear DNA-nanocomponent constructs can be utilized as photonic and/or electronic wires and organized into a variety of useful integrated networks, circuits and devices. This invention includes the unique higher order photonic/electronic devices, and other anticipated higher order integrated devices, structures and materials which can be created from the resulting first order nanostructures of the process.

In accordance with the discussion above, in one embodiment, the present invention relates to a system for controlled fabrication of a functionalized nanostructure comprising: a) a first chamber containing a solution of polymers derivatized with a first binding partner at regular intervals; b) a nanopore structure with a plurality of defined nanopores therethrough; c) a second chamber in fluid communication with the first chamber through the nanopore structure containing a solution of nanocomponents derivatized with a second binding partner that binds to the first binding partner, wherein the nanocomponents are prevented from passing through the nanopores; and d) a source of a driving force adapted for facilitating movement of the polymers in the first chamber through the nanopores into the second chamber within which the second binding partner binds to the first binding partner to form the functionalized nanostructure with the nanocomponents bound to the polymer at predetermined intervals.

The polymers may be, for example, nucleic acids (such as DNA, RNA or a DNA/RNA copolymer), modified polynucleotides (such as pNA, a nucleic acid with a non-ribose sugar, or a nucleic acid containing modified bases), polysaccharides (such as polydextran, starch, glycogen or cellulose), inorganic polymers (such as glass fibers, carbon fibers and siloxane fibers), organic polymers, proteins (such as enzymes, antibodies and polypeptides), and synthetic macromolecules (such as dendrimers, fullerenes, crown ethers, micelles and liposomes).

The first binding partner and the second binding partner may be, for example, complementary nucleic acids, epitopes and antibodies, ligands and proteins, biotin and streptavidin, chemically reactive entities, or metal ions and a metal ligands.

The nanopore structure may consist of an organic porous membrane (such as an agarose gel, a polycarbonate membrane or a polyacrylamide gel) or an inorganic porous membrane (such as glass and silicon structures.

In another embodiment, the present invention relates to a process for controlled fabrication of functionalized nanostructures in an apparatus, wherein the process comprises the steps of: a) placing a solution containing polymers derivatized with a first binding partner at regular intervals into a first chamber; b) placing a solution containing nanocomponents derivatized with a second binding partner that binds to the first binding partner into a second chamber in fluid communication with the first chamber through a nanopore structure with a plurality of defined nanopores therethrough, wherein the nanocomponents are prevented from passing through the nanopores; and c) subjecting the apparatus comprising the first chamber, the second chamber and the nanopore structure to a driving force that facilitates the movement of polymers in the first chamber through the nanopores into the second chamber, wherein the second binding partner binds to the first binding partner to form the functionalized nanostructure with the nanocomponents being sequentially bound to the polymer at regular intervals along the length of the polymer.

The driving force may be electrical, chemical and/or physical in nature, as generated by a pair of electrodes, a chemical gradient, or a pump, thermostat, or vacuum, respectively.

In addition, the nanostructure may further include a catalyst attached at or near the nanopores.

In still another embodiment, the present invention relates to a plurality of functionalized nanostructures, each comprising at least two different nanocomponents sequentially attached to a polymer at regular intervals in a predetermined pattern and order. The attachment is by formation of a bond between the nanocomponents and the polymers (which may be the result of a chemical reaction in addition to the formation of a more conventional binding partner such as antibodies and antigens binding to each other.)

The nanocomponents attached to the nanostructures may, for example, be quantum dots, metallic nanoparticles, semiconductor nanoparticles, polymeric nanoparticles, carbon nanotubes, nanorods or nanowires. In addition, the nanostructures may also have sheathing particles attached thereto which includes, for example, organic polymer nanoparticles, metallic nanoparticles and refractive index influencing nanoparticles.

The functional nanostructures may also comprise cleavage sites at predetermined intervals along the polymer, such as endonuclease cleavage sites when the nanostructure comprises a nucleic acid.

In yet another embodiment, the present invention relates to a method for controlled fabrication of functionalized nanostructures comprising: a) providing a solution of polymers derivatized with a first binding partner at regular intervals in a first chamber; b) providing a solution of nanocomponents derivatized with a second binding partner that binds to the first binding partner in a second chamber; and c) contacting the polymers with the nanocomponents through a nanopore structure having a plurality of controlled permeability nanopores separating the first chamber and the second chamber, wherein the nanocomponents attach to the polymers in a predetermined pattern and order.

Other aspects of the invention are discussed throughout the specification.

DETAILED DESCRIPTION OF THE INVENTION

Figure 1:
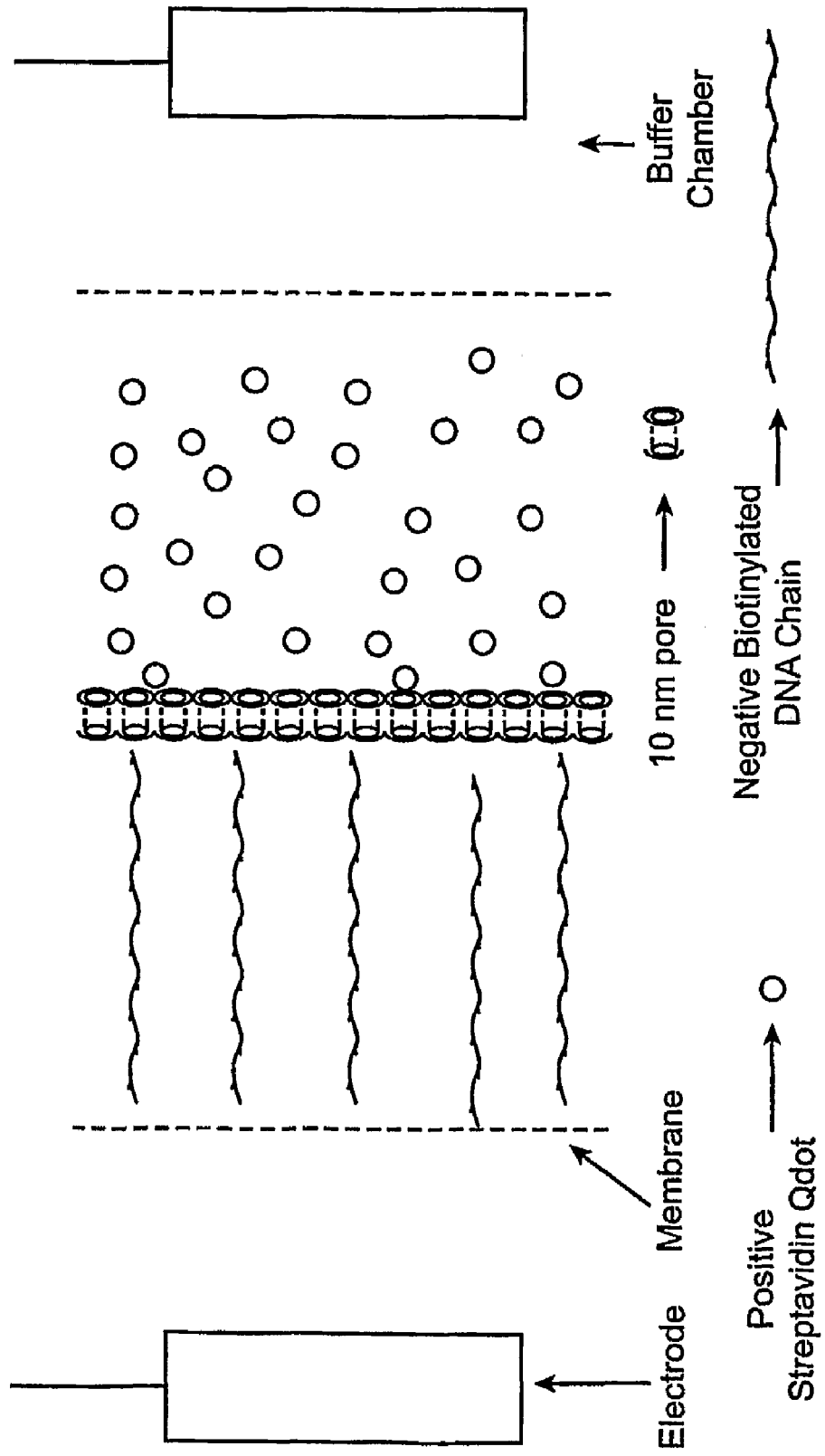
FIG. 1—Shows the basic concept for an electric field based compartmentalized nanopore device and the process which can be used to carry out the controlled fabrication of higher order nanostructures from multiply functionalized molecules and multiply functionalized nanostructures. In the first phase, specific DNA sequences which has been derivatized with biotin moieties at selected positions along its backbone structure are placed in the left hand chamber. Nanoparticles with multiple functionality (streptavidin quantum dots) are placed in the right hand chamber of the device. A nanopore membrane (polycarbonate) with 10 nanometer pores separates the two chambers. The biotin-DNA sequences in the left chamber have a net negative charge, and the streptavidin-quantum dots can be either neutralized or given a slight positive charge by adjusting the pH of the solution. A DC electric field strong enough to produce electrophoretic propulsion of the negatively charged DNA is now applied to the system, negative bias to left electrode and positive bias to the right electrode.

The invention relates to processes and devices for the controlled fabrication of nanostructures from starting components that have high fidelity recognition properties and multiple binding groups. In one embodiment, the invention relates to the formation of nanostructures using controlled sequential addition of nanocomponents at regular intervals via sequential formation of binding pairs or other chemical binding reactions.

Starting components can include multiply functionalized DNA sequences, polymers, proteins, quantum dots, metallic nanoparticles, and carbon nanotubes. Starting components with high fidelity recognition properties and multiple binding groups are held in separate chambers separated by a defined nanopore membrane structure (i.e., a "nanopore structure") having a controlled pore size, pore shape, pore spacing and/or pore length (collectively referred to herein as "pore morphology".) A group of multiple binding components in one chamber are transported through the nanopores in the nanopore structure into the second chamber containing a second group of multiple binding components. The controlled emergence of the first multiple binding components into the chamber containing the second multiple binding components allows the two components to bind or react in the desired sequential fashion.

The devices and techniques of the invention allow unique nanostructures to be synthesized and assembled without the use of complex chemical blocking procedures and with greatly reduced non-specific intermolecular and intramolecular binding reactions. Related nanopore processes also enable high resolution separation of final nanostructures from the starting components. The devices and techniques of the invention allow for the creation of higher order nanophotonic and nanoelectronic structures; photovoltaic and biohybrid photosynthetic antenna nanodevices; hybrid intermetallic fuel cell catalysts and battery nanodevices, multiple enzyme reaction chain nanodevices for diagnostics, therapeutics and bioprocesses; and other unique two and three dimensional heterogeneous/hybrid nanodevices and nanomaterials.

As described, in its most broad context, this invention relates to devices, processes, techniques and methodologies which allow for the controlled synthesis, assembly, organization, or fabrication of unique complex higher order two and three dimensional macromolecular structures, microstructures and macroscopic sized structures from starting components that have high fidelity recognition and multiple chemically reactive or ligand binding groups that, when combined together as described herein, form nanostructures with nanocomponents attached thereto at regular intervals.

High fidelity recognition polymeric starting components include, but are not limited to, multiply functionalized biopolymers such as DNA, RNA, synthetic polynucleotides and oligonucleotides, peptide nucleic acid (pNA) and other linkage sugar or base modified nucleic acids; proteins (which includes synethetic and/or naturally occurring polypeptides and oligopeptides), nanotube structures and combinations of polymeric substances, such as mixed peptide and oligonucleotide sequences. Other polymeric starling components include, but are not limited to multiply functionalized biopolymers such as polysaccharides, oligosaccharides and polydextrans; organic polymers such as polyethylene glycols (PEGs), polycarboxylic acids and polyamines; inorganic polymers and glass micro/nanofibers; biomolecules such as proteins, enzymes and antibodies; synthetic macromolecules such as dendrimers, fullerenes, cyclodextrans, crown ethers, micelles and vesicles. The polymer may also be a nanotube.

The nanocomponent starting material includes, but is not limited to, quantum dots, metallic nanoparticles, semiconductor nanoparticles, polymeric nanoparticles, carbon nanotubes and other nanotube, nanorod and nanowire structures.

The binding or reaction between components can involve the formation of binding pairs from corresponding binding partners attached to the two different components, or through the formation of attachments via chemical reactions therebetween. As used herein, the term "binding partner" refers collectively to both situations, such that it refers to both a member of a binding pair, as well as either one of two "participants" in an attachment-forming chemical reaction (such as a nucleophile and an electrophile). Examples of chemically reactive pairs that react with one another either directly or by activation in the presence of another reagent such as a catalyst include, for example, amine/aldehyde, amine/succinimidyl esters, amine/isothiocyanates, amine/terafluorophenyl esters, amine/sulfonyl chlorides, thiol/maleimides, thiol iodoacetamides, aldehyde/hydrazines, aldehyde/hydroxylamines, hydroxyl/carboxyl (with a carbodiimide coupling agent), amine/carboxyl (with a carbodiimide coupling agent). Other reactive groups are well known in the chemical arts.

Accordingly, both the polymer and nanocomponent starting materials are multiply functionalized to include, without limitation, high fidelity recognition components and other components which contain chemically reactive groups such as amine, carboxyl, aldehyde, and sulfhydral groups or combinations of such chemically reactive groups; and to components that contain ligand binding groups such as biotin/streptavidin, antibody/antigen, metal chelating or coordination structures, metal ligands or metal complexing reactions, or combinations of those binding groups. Components which contain combinations of both chemical binding and ligand binding groups are also anticipated by the invention. Chemical binding groups are those which will ultimately result in a preferably covalent bond being formed between components. Ligand binding reactions are those which will result in a so-called non-covalent bonding between components. Such ligand binding/non-covalent binding can be the result of hydrogen bonding, hydrophobic binding, electrostatic binding, Van der Walls interactions, chelation and/or combinations of such interactions.

The basic process of this invention involves placing multiply functionalized components (with multiply reactive groups) into separate fluidic chambers separated by a nanopore structure with "defined" nanopores transversing the structure having a predetermined morphology (e.g., size and shape) and pattern (e.g., spacing, arrangement). Such nanopore structures and the chambers they separate can be macroscopic, microscopic and/or nanoscopic in one or more of their dimensions. Multiple chambers can be placed in series arrangements, each separated by a nanopore structure such that the chambers are in "fluid communication" through the nanopore structure, which means that the solution in which the components are placed in the separate chambers is free to traverse the nanopore structure. In one example, viscosifiers which are known in the art can be included in one or more of the solutions to alter the transport properties of the various system components through the nanopores. In another example, some components of the system, such as water, may be able to pass through the nanopore structure itself, as well as through the nanopores. The nanopore structure may consist of a membrane, thin film or any nanopore-containing structure made of a variety of other materials.

When the driving force that facilitates the selective movement of components through the nanopores is electrical, electrode elements are placed in the end chambers so as to enable the production of an appropriate electrophoretic field to transportions and components to and from the different chambers. Other electrodes can be placed in the internal chambers to achieve auxiliary transport effects. The main DC field can be applied in a continuous, ramped or pulsed mode so as to produce the desired electrophoretic and/or electroosmotic transport. The DC field can be sourced as either voltage or current. The amount of voltage or current would depend to some extent upon the characteristics of the device, such as the nanopore morphology and pattern, the size of the nanopore structure, etc. Generally, voltages may range from several volts to 100's of volts for miniature devices (5 mm×5 mm×20 mm or smaller); to 10's volts to 1000's of volts for midsize devices (around 5 cm×5 cm×20 cm); and from 100's to 10,000 volts for large devices (50 cm×50 cm×200 cm or larger). For adverse heating effects that might be caused by the application of higher voltages, cooling systems can be incorporated into the device structure. The electric field polarity can also be alternated so as to produce a net transport in one direction, but some reverse transport in the opposite direction. Such a process can reduce pore clogging and to help orient linear structures for more effective transport through the narrow pores. Pressure, pumping and or centrifugation can also be used in certain cases to transport components from one chamber to another.

In another aspect related to the device and process, auxiliary electrodes may be place so as to produce electric fields which run horizontal to the plane of the nanopore structure. If the primary electric field which transports components through the nanopores is designated as the Z-direction, then the auxiliary fields would be horizontal to the direction of the nanopores and considered the X and Y directions. Such auxiliary electrodes would be beneficial in aiding in the transport of the linear components through the nanopore structure. It is also anticipated by this invention that alternating electric fields (AC) can also be used in the device. It is further anticipated that pressure, pumping and or centrifugation can be used in addition to or in combination with electric fields as the driving force to facilitate the transport of components through the nanopores from one chamber to another.

Figure 7:
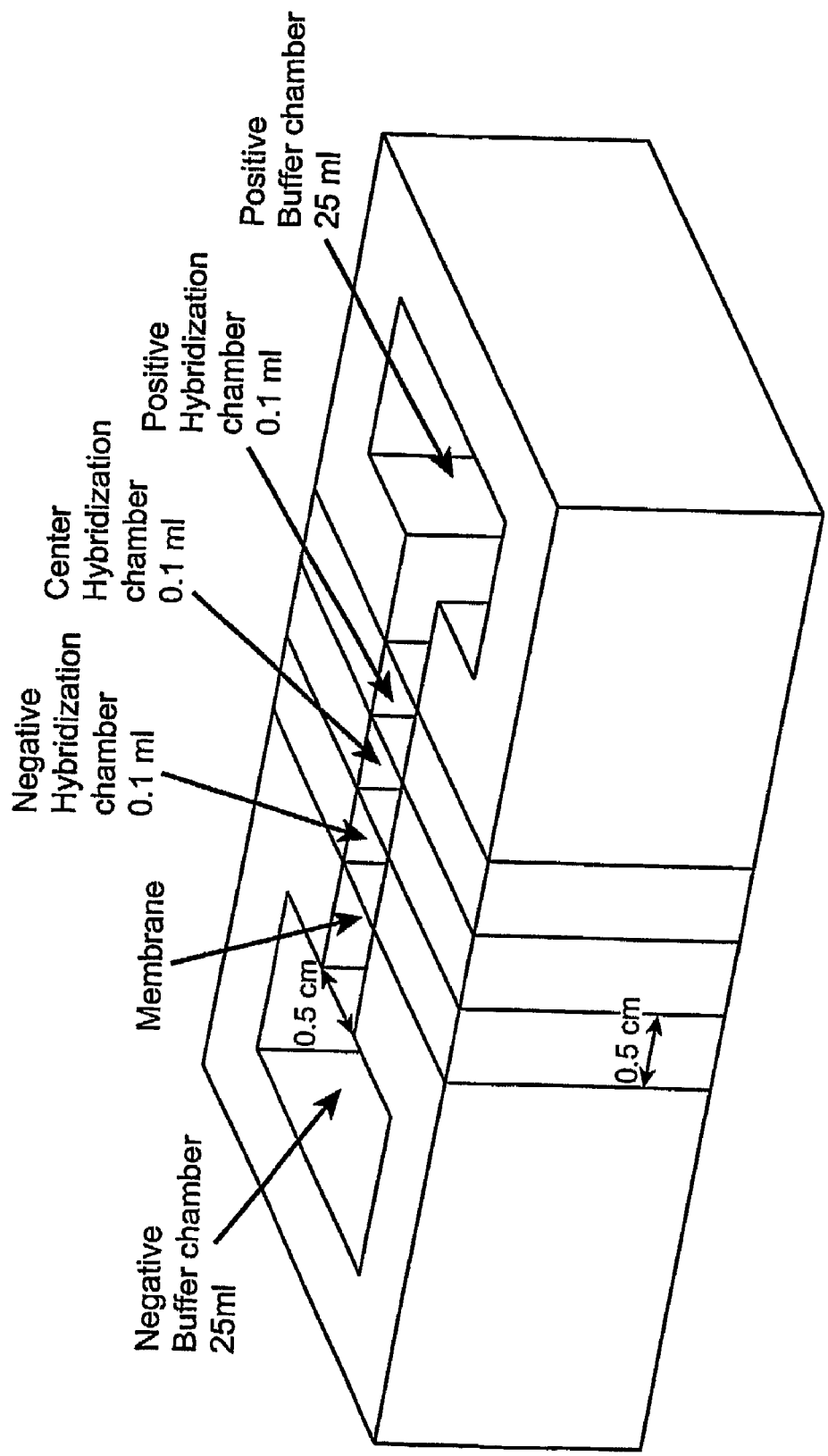
FIG. 7—Shows a genetic diagram of a multichambered nanopore device used to carry out the nanopore synthesis process.

FIG. 7 shows a picture/diagram of a simple chambered nanopore device. Nanopore structures include but are not limited to porous membranes (polycarbonate), porous gels (agarose, polyacrylamide, etc.), porous glass or porous silicon structures with defined nanopores. Such nanopores can also be modified to enhance or improve their transport and/or selective properties. In one aspect, nanopore structures can be modified to reduce or enhance their electroosmotic properties, i.e., to transport liquid (water) through the pore in one direction, while counter ions and/or certain nanocomponents move in an opposite direction. A general scenario for the nanopore process may involve placing a first group of multiply functionalized charged (net negative or positive) components in one chamber of the device, and applying an electric field so as to actively transport (electrophorectically and/or electroosmotically) the charged components through the defined nanopores into the second chamber containing a second group of multiply functionalized components. The second group of components can be either neutral, charged or of such shape or size that they are not able to readily pass through the nanopore membrane into the first chamber. The controlled emergence of the first multiply functionalized components into the chamber containing the second multiply functionalized components allows the two components to selectively react or bind in a predictable sequential fashion favoring assembly into the desired nanostructure. In a further aspect of the process, the device can be designed so that the newly assembled nanostructures in the second chamber can now be transported from that second chamber through another membrane (with larger pore size) into a third chamber. This process allows the assembled nanostructures to be separated (purified) form the un-reacted components in the second chamber. Overall, the nanopore device and process greatly minimizes or eliminates the competing and undesirable nonspecific intermolecular and intramolecular cross linking reactions which would occur if the components were simply mixed together.

In one aspect, this invention relates to a controlled bottom-up self-assembly nanofabrication process utilizing electrophoretic transport and a chambered nanopore device with an arrangement of nanopore membrane structures and compartments. The process and nanopore device can be used to control the self-assembly, organization, specific modification, synthesis, and fabrication of higher order nanostructures form high fidelity recognition multiply functionalized biopolymer components with multiply functionalized nanoparticle components. High fidelity recognition multiply functionalized biopolymer molecules can include multiply functionalized DNA, RNA, PNA (peptide nucleic acids), polynucleotides, oligonucleotides, polypeptides, or other self-assembling biomolecules, synthetic structures or combinations thereof. Multiply functionalized nanoparticles and components can include functionalized quantum dots, metallic nanoparticles, polymeric nanoparticles, or nanotube structures. Using the chambered nanopore device of the invention, a first set of high fidelity recognition multiply functionalized biopolymer molecules can be reacted in a controlled sequential fashion with a second set of multiply functionalized nanoparticles to form a viable higher order nanostructure. Using the intrinsic high fidelity recognition properties of the first order nanostructures created by the device, these nanostructures may now be further self-assembled into larger two or three dimensional higher order structures, materials and devices with microscopic or macroscopic dimensions. Furthermore, any of the available un-reacted binding sites on the first order structures may be now reacted with other appropriate binding moieties or elements.

Figure 2:
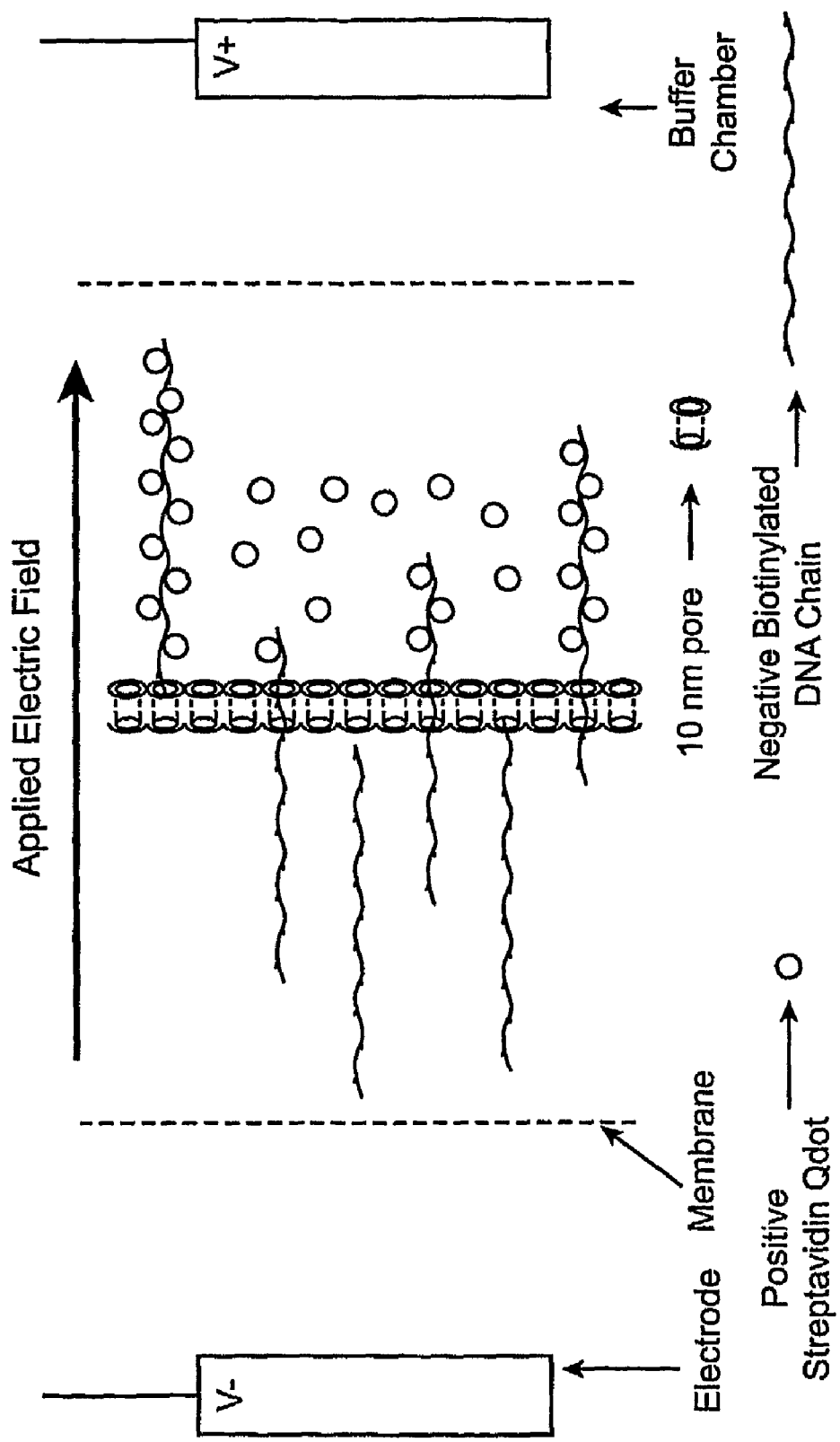
FIG. 2—As the DC field is applied to the system the negatively charged biotin-DNA molecules begin to move through the 10 nanometer nanopores into the chamber containing the streptavidin-quantum dots. As each biotin moiety on the DNA sequence exits the nanopore, it immediately binds a streptavidin-quantum dot. However, the electric field keeps the negatively charged DNA molecules extended and moving toward the positive electrode, making it difficult for the DNA molecule to flex backwards and crosslink it's bound streptavidin-quantum dot to another un-reacted biotin exiting from the nanopore, thus eliminating the potential for both inter and intramolecular cross linking.
Figure 3:
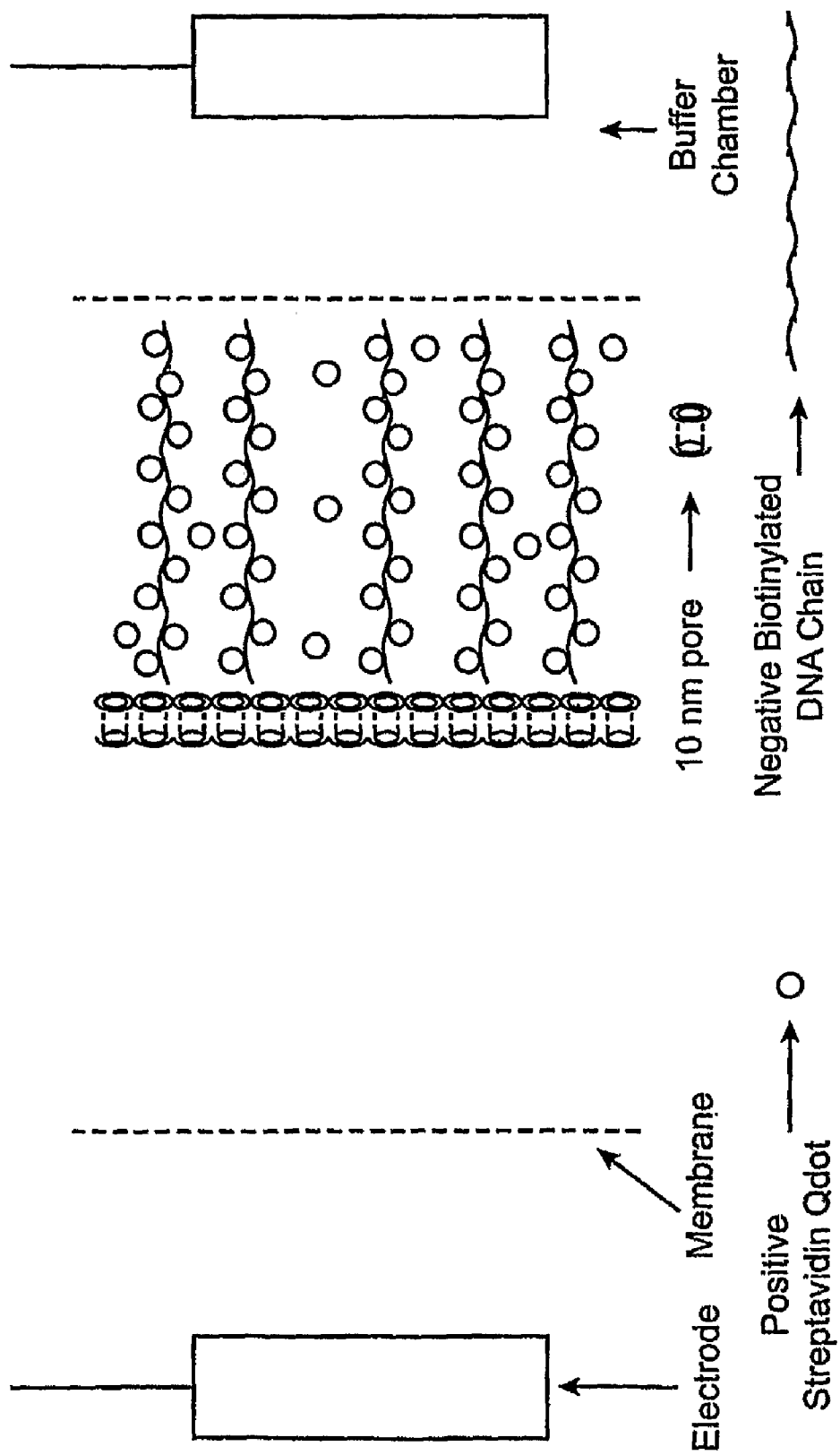
FIG. 3—Shows the final stage of the process where the biotin-DNA strands have now been completely functionalized with streptavidin-quantum dots. It should be again pointed out that the quantum dots now bound to the DNA sequence still have remaining streptavidin molecules and binding sites which may be used for further modification of the higher order structure. Also, because the intra and intermolecular cross linking has been eliminated, the linear DNA-quantum dot structures remain viable for further self-organization based on high fidelity hybridization.

By way of further example, this invention teaches how a multiply functionalized DNA sequence and multiply functionalized nanoparticle (quantum dots) components can be processed through a nanopore chambered device so as to produce high molecular weight linear DNA constructs with multiply functionalized nanoparticles attached at precise locations along the DNA back bone structure. Multiply biotinylated double-stranded DNA sequences and streptavidin derivatized quantum dots are placed into separate fluidic chambers separated by a defined (10 nanometer pore size) nanopore membrane structure. A DC electric field is now applied to the chambered nanopore device. The negatively charged multiply biotinylated ds-DNA molecules in the first chamber are transported (electrophoretically) through the nanopores into the second chamber containing the streptavidin-quantum dots. The controlled emergence of the multiply biotinylated ds-DNA sequences into the second chamber containing the streptavidin-quantum dots allows the two components to react or bind in a predictable sequential fashion favoring assembly of the desired linear ds-DNA-quantum dot nanostructures. FIGS. 1-3 show the initial step, intermediate steps and final stages of the electric field nanostructure fabrication process. A key benefit of this process is that the competing nonspecific intermolecular and intramolecular cross linking reactions are greatly minimized or eliminated. That is, the nanopore process greatly reduces the chances that an emerging biotinylated DNA strand has an opportunity to fold back on itself and allow one of its un-reacted quantum dot streptavidin binding sites to react with a newly emerging un-reacted biotin on its backbone structure, i.e., this prevents intramolecular cross linking. Additionally, the appropriate spacing of the nanopores now prevents any of the emerging biotinylated DNA strands from interacting with each other until their newly emerged biotin has reacted with a free streptavidin quantum dot, i.e., this prevents intermolecular cross linking between the different DNA strands.

Figure 4:
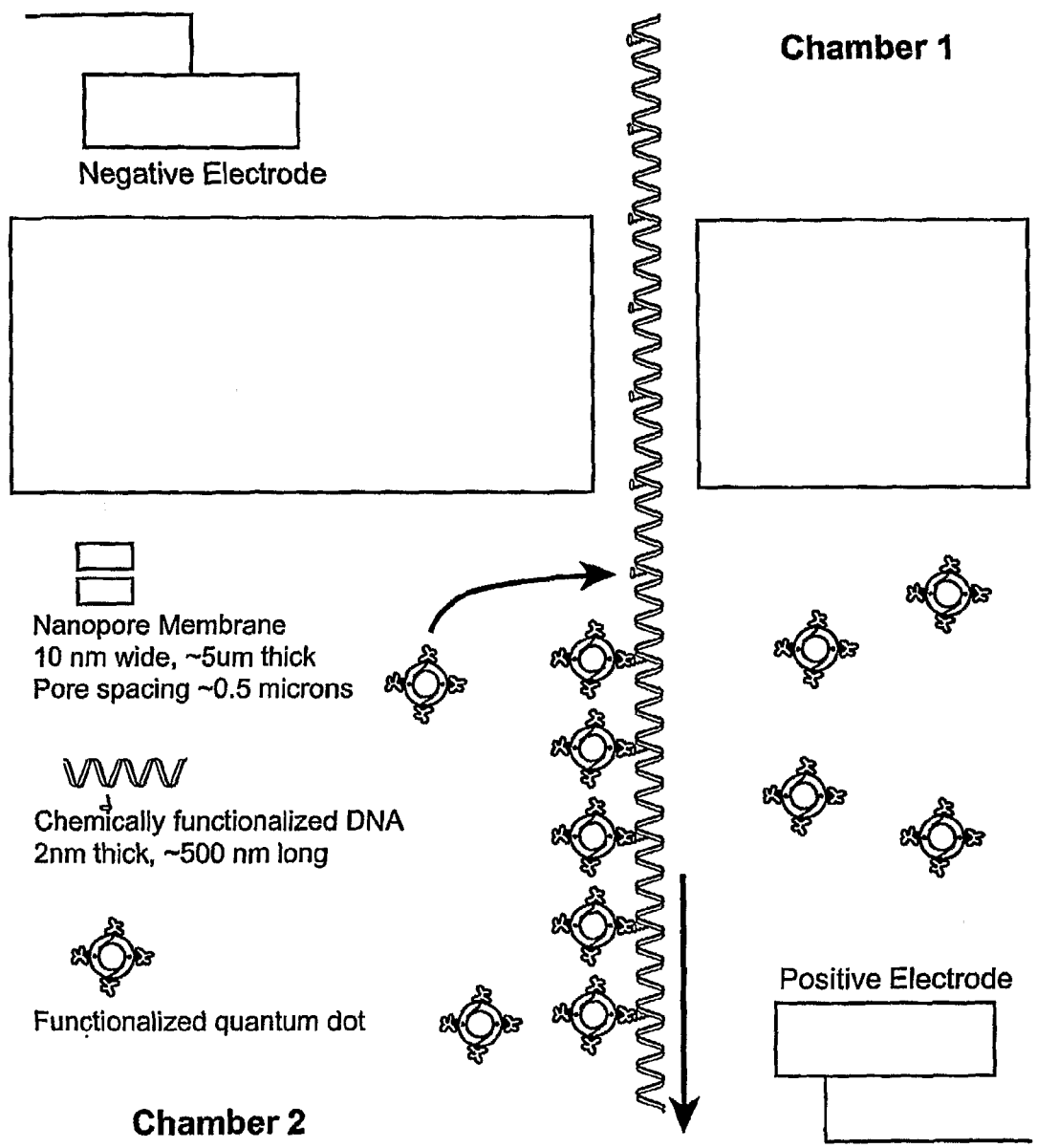
FIG. 4—Shows in more detail a multiply biotinylated DNA sequence moving through a 10 nanometer nanopore in response to an applied DC electric field. The DNA is a double helix about 2 nm in diameter. The nanopore itself is 10 nm in diameter. The biotinylation sites are spaced at every 34 bases along the DNA sequence, which spaces them by about 12 nm. The streptavidin quantum dots are approximately 10-15 nm in diameter. This controlled exit of the biotinylated DNA sequence and the nanopore spacing greatly reduce the competing non-specific intermolecular and intramolecular cross linking reactions which would otherwise take place.
Figure 5:
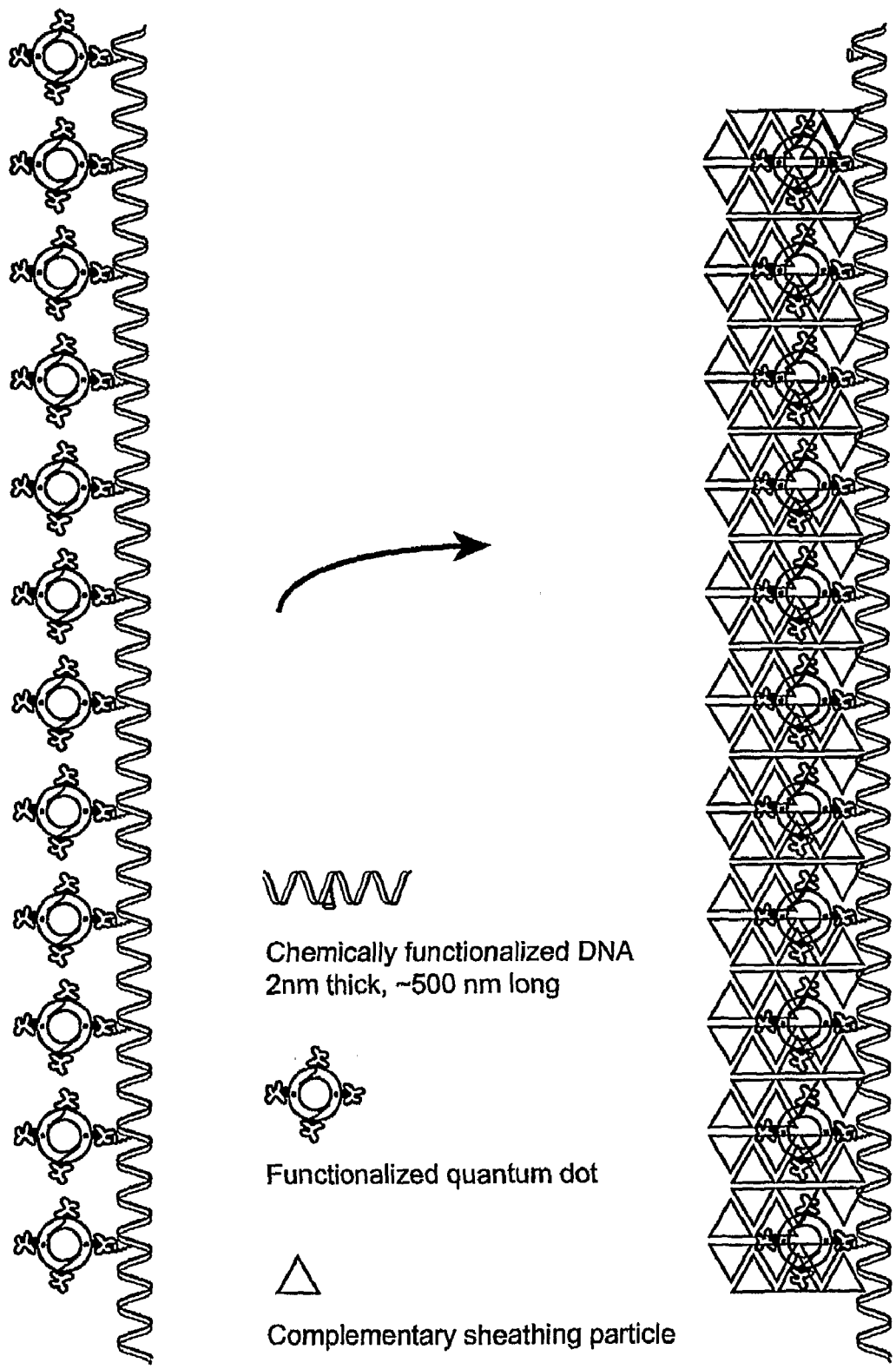
FIG. 5—Shows how the linear DNA-quantum dot nanostructures from the process can now be further derivatized by reaction of the remaining streptavidin functional groups (on the quantum dots) with an appropriate biotinylated moiety to sheath the DNA-quantum dot nanostructure. This sheathing process is used to reduce quenching, and to improve the overall photonic transfer efficiency, robustness and other performance properties of the DNA-quantum dot nanostructure.

FIG. 4 shows a more detailed view of the biotinylated DNA sequence emerging from the nanopore and how the reaction with streptavidin quantum dots is controlled. Once the nanostructures are formed, these linear ds-DNA-quantum dot structures can now be further derivatized to form higher order structures by reaction of the remaining streptavidin functional groups (on the quantum dots) with appropriate biotinylated moieties to sheath the DNA-quantum dot structure. FIG. 5 shows the sheathing of the linear DNA-quantum dot nanostructure which is carried out to reduce quenching, and to improve the photonic/electronic transfer efficiency, robustness and other performance properties of the nanostructures. Subsequently, the high fidelity base pairing recognition properties within the DNA-quantum dot nanostructures can be used for further self-assembly (via hybridization) of the first order nanostructures into higher order interconnected structures. Thus, the first order DNA-nanoconstructs (i.e. the nanostructures) can be utilized as photonic and/or electronic wires and organized into a variety of useful integrated networks, circuits and devices. This invention includes the unique higher order photonic/electronic devices, and other anticipated higher order integrated devices, structures and materials which can be created from the resulting first order nanostructures produced by the nanopore process. Accordingly, exemplary sheathing systems include attaching organic polymer nanoparticles for sheathing electronic or electrical conduction properties, attaching metallic nanoparticles for sheathing and enhancing photonic transfer properties, and attaching refractive index altering nanoparticles for enhancing photonic transfer properties.

Figure 6:
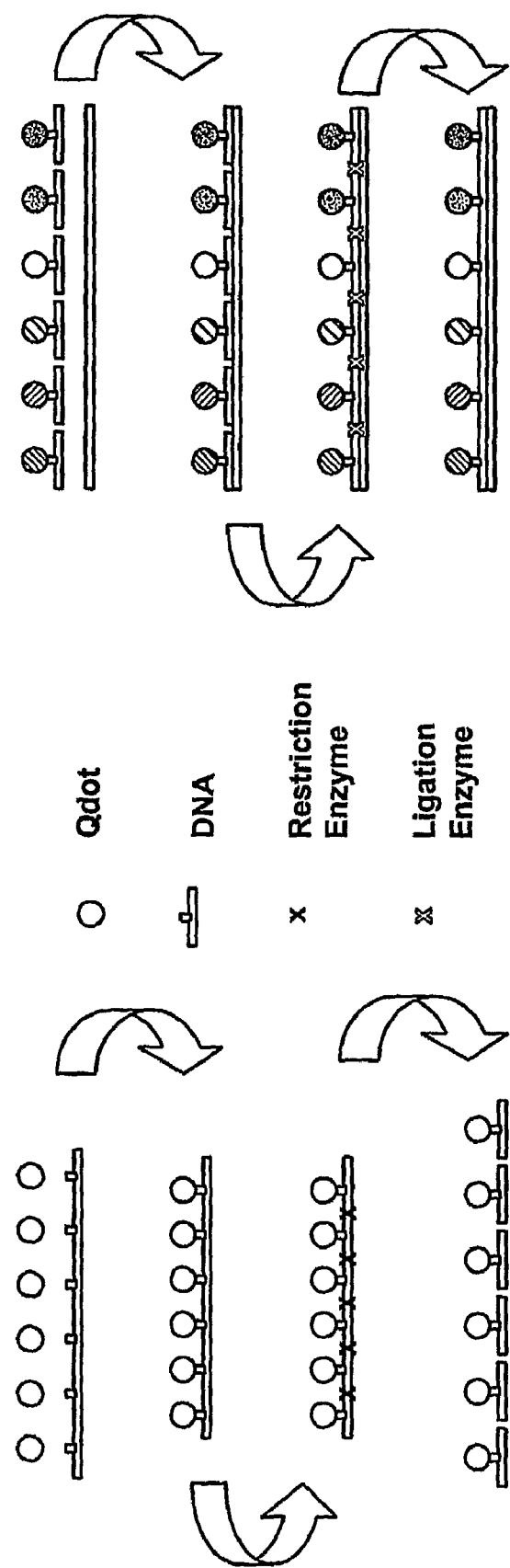
FIG. 6—Shows a diagram of how the primary electric field nanopore process can be used to assemble individual sets of linear double-stranded DNA nanoparticle or nanocomponent DNA structures each of which have a different type of nanoparticle or nanocomponent on the DNA backbone. The DNA structures are different repeated DNA sequences containing one or more specific restriction cleavage site. After carrying out the nanopore reaction process to attach specific nanoparticles to the different DNA sequences, the DNA strands can then be specifically cleaved by the appropriate restriction endonuclease into individual segments containing the one type of nanoparticle or component. Complementary template strands of DNA can now be designed and synthesized to which any given combination of the different DNA nanoparticle segments can be rehybridized. This unique secondary process allows the creation of any desired linear combination of nanoparticles and/or nanocomponents on a template DNA sequence.

Another related aspect of this invention includes the use of the primary electric field nanopore process to assemble individual sets of linear double-stranded DNA/nanocomponent structures, each of which have a different type of nanocomponent on the backbone structure (FIG. 6). In this process, the DNA structures each contain a different repeated DNA sequence, which is designed to contain one or more specific restriction enclonuclease cleavage sites. After carrying out the nanopore reaction process to attach specific nanocomponents to the different DNA structures, the DNA strands are then treated with the appropriate restriction endonuclease enzyme which cleaves the larger DNA strands into individual segments containing a nanocomponent. Longer complementary template stands of DNA can now be designed and synthesized to which any given combination of the different DNA nanocomponent-containing segments can be rehybridized. This unique secondary process allows for the creation of any desired linear combination of nanocomponents onto a template DNA sequence. Additionally, the remaining reactive binding components on the structures may be further modified, and the DNA strands may be further assembled or interconnected into higher order structures, materials and devices.

In yet another aspect of the invention, the use of a combined electrophoretic/electroosmotic nanopore process allows linear mono and di-derivatized DNA nanoconstructs to be separated from starting nanoconstructs and nonlinear DNA/nanoconstructs. In this process, a first chamber is filled with multiply functionalized nanoconstructs, such as streptavidin quantum dots, and a biotinylated DNA sequence such as a 3' or 0.5° terminally biotin labeled oligonucleotide. The reaction is allowed to proceed so as to react the biotinylated oligonucleotides with the strepatavidin quantum dots, producing mono, di, tri and other multiply labeled oligonucleotide-quantum dots. An electric field is now applied to the nanopore device to the degree which allows the oligonucleotide-quantum dots to be more rapidly transported through the nanopores, while the less charged un-reacted quantum dots are less efficiently transported. Additionally, the un-reacted less charged quantum dots are also prevented from going through the nanopores by the opposing electroosmotically driven flow of liquid through the nanopores. The more highly charged linear mono- and diderivatized oligonucleotide-quantum dot constructs are able to move through the nanopores into the second chamber (even against the electroosmotically driven flow). Any of the charged larger multiply derivatized oligonucleotide-quantum dot nanostructures are prevented from moving into the second chamber by the nanopore size/morphology exclusion.

In another aspect of the invention, the nanopore process can be used in such a way so that molecules (small, linear, or polymeric) which are passing through the nanopore can be selectively modified in a serial fashion by a reactive catalytic molecule (such as an enzyme) which is immobilized or positioned at the nanopore entrance or exit. In one possible variation, a linear template molecule may be passed through the nanopore structure from which other structures may be synthesized. An example of this is to use a template DNA or RNA sequence transported through the nanopore, where a polymerase adjacent to the pore exit is able to build a complementary DNA or RNA strand. It is further envisioned that multiple catalytic molecules or enzymes can be substituted for polymerase. It is also further envisioned that a series of such reactive nanopore structures may be coupled together to carry out highly complex synthesis and modification of molecular structures.

Novel linear combinations of heterogeneous nanocomponents that are re-assembled onto template DNA sequences can be used to create a number of new higher-order structures, materials and devices that include:

(1) Heterogeneous nanophotonic and nanoelectronic transfer structures, such as multiple donor/acceptor fluorescent resonant energy transfer (FRET), electron transfer and hybrid FRET/electron transfer [D1+n–D2+n–D3+n–A1+n] structures. In such systems D1, D2, and D3 and A1 can represent donor and acceptor moieties with different excitation/emission properties or electron transfer properties; different types of donor and acceptor and/or electron transfer moieties (organic chromophores, fluorophores, electron transfer molecules; fluorescent and electron transfer proteins; metal chelates; fluorescent organic polymer nanoparticles; quantum dots, metallic nanoparticles, dendrimers, and further derivatized or functionalized versions of said moieties). In addition to nanophotonic and nanoelectronic transfer, logic and data storage applications; such higher-order structures could be used for high efficiency photovoltaics (improved antenna structure, charge separation properties, photonic to electron conversion efficiency, and electronic to chemical energy conversion).

(2) Highly networked and interconnected two and three dimensional structures with predictable shapes and geometries. By incorporation of secondary binding and recognition properties (DNA sequence, protein, ligand, etc.) into selected positions on the initial linear heterogeneous nanostructures, predictable two and three dimensional higher-order structures can now be created by repeating the nanopore synthesis process. By way of example, a linear heterogeneous nanostructure transported through a larger nanopore could now be selectively reacted with complementary DNA nanostructures which would bind to the core linear structure in a radial fashion. Such a process and the resulting next level of higher-order structures and components could be useful in the construction of even more highly integrated photonic and electronic materials and devices (neural network type logic, date storage, photonic energy collection and conversion materials and devices); as well as for highly integrated nanocomposite materials with improved properties, including nano-thread and micro-thread structures for producing fabric like nanocomposite materials.

(3) Linear catalytic structures for sequential chemical processing, conversions, and for the nanomechanical transport of nano and microscale entities. In this case, the initial nanocomponents with different catalytic moieties (metallic catalyst, inorganic/ceramic catalyst, enzyme catalyst and combinations) are re-assembled in a controlled and predicable fashion onto a template DNA sequence. This process will now allow the creation of a wide variety of nano-scale chemical factories for processing biological, organic, polymeric and inorganic substances which require multiple reaction steps. These processes can include the degradation of a substance or material (cellulose or starch to glucose), the interconversion of a substance or material (starch to glucose to ethanol), or the synthesis of a substrate into a higher-order product or material (drug, polymer, macromolecule, etc.). Such processes would be very useful for the synthesis of unique biomaterials, biopolymers, heteropolymers and drugs; for bioenergy conversions and for removal (degradation) of toxic and waste substances of environmental concern. In is also within the scope of this invention to create linear sequences of enzymes (ATP synthase, dynesins, kinesins, actins, etc.) which produce mechanical or dynamic transport properties. In this case, one could create linear structures for the transport of nano- and microcomponents to and from various locations; for ion and fluid pumping (when combined with membrane nanopore structure); nanomechanical structures with dynamic properties (walking, crawling, rotating, oscillating, etc.); and for producing smart morphing nanocomposite materials.

Finally, it is within the scope of this invention that combinations of one or more of the processes, techniques, structures or products discussed above can be combined into other novel and useful applications related to highly integrated materials, devices and systems.

EXPERIMENTS

Experiment 1

The purpose of this procedure is to create long chains of quantum dots on a DNA substrate, spaced at regular but short (~10-20 nm) intervals, in a defect free manner. This process involves 2 separate steps. The first is to create the DNA backbone upon which the quantum dots will be attached by taking synthetically created, chemically functionalized DNA subunits, and putting them together using standard DNA biochemistry enzymatic techniques (ligation). The second process is to take the synthetic, functionalized DNA backbone, and to further functionalize it with quantum dots in a manner that eliminated inter- and intra-construct crosslinking. This is necessary because both the quantum dots and the backbones are multiply functionalized.

The ligation procedure is an enzymatic process where two adjacent DNA strands become chemically linked as if they were one unbroken piece of DNA, with the link being the same as between any two adjacent DNA bases. Our system involves two synthetic pieces of DNA (A and B) that can hybridize to each other in two different ways. That is, the front of Type A DNA will bind to the back of Type B DNA while the front of type B will hybridize to the back of type A. Since each piece of DNA can bind to two other of the opposite type, the resulting structure is a chain of alternating type A and B DNA. Since these starting fragments call have chemical groups located on them, the longer chain will have these chemical groups located at regular intervals, as the structure necessarily repeats regularly. The use of ligation will chemically fuse the breaks in the DNA that would occur at each segment so as to prevent it from dehybridizing under marginally harsh conditions that larger DNA strands of ligated material would be able to withstand, The current method for creating the larger DNA fragments is as follows:
1. Mix an equal amount of type A and B DNA together in solution (concentration is a about $5 \times 10^{-6}$ molar).
2. Take 1 ul of the solution, and mix with Ligase, ligation buffer, and ATP (amounts to be determined from directions). These materials can be purchased as a kit in proper proportions.
3. Mix the mixture well and let it sit at room temperature overnight.
4. Various methods can be used to modulate the total length of the final product.

Such methods include starting ratio and concentration of DNA monomers, length of ligation time, chemical parameters of the ligation kit, and the length of the monomer segments. The final result is a spectrum of DNA backbones of various lengths. These backbones can be separated using gel electrophoresis on a low strength agarose gel.

5. Once the Backbones are separated by length on a gel, the band of desired length is cut out of the gel, and the gel removed through standard purification techniques. The DNA backbones are dissolved in water for the next phase of the experiment.

The next phase of the procedure is to create the final structure consisting of the DNA backbone modified with regularly spaced quantum dots. The linkage used is a biotin/Streptavidin reaction, with the DNA having regularly spaced Biotin and the quantum dots being coated in various amounts of Streptavidin. Direct mixing of the backbones and the quantum dots would lead to a quantum dot binding to multiple biotins, either on one Backbone, or on several different backbones. To eliminate these crosslinking processes, we pass the backbones through a porous membrane to keep them physically separated from each other (to prevent inter-backbone crosslinking) and to keep them straight (to prevent intra-backbone crosslinking). The membranes used are Polycarbonate rack etched (PCTE membranes). The membrane is also able to keep the quantum dots separated from the initial solution containing the backbones by size exclusion if the proper pore sizes are chosen. Since the width of the DNA is ~2 nm (though the length is much longer), and the width of the quantum dots is ~10-20 nm, it is possible to send DNA through one way, but to keep the quantum dots from crossing over in the other direction.

The device for doing this consists of several chambers separated by membranes. In its simplest form, the device is two large buffer chambers on the outer ends of the device, connected to two smaller hybridization chambers in the middle. The membranes would all have 10 nm sized pores.

The buffer chambers would each have an electrode, with one ultimately to be the negative one, while the opposite chamber would be the positive. The adjacent hybridization chambers are called the negative and positive hybridization chambers. The buffer chambers are of arbitrary size, holding at least 25 ml of buffer. The hybridization chambers are roughly 5 cm in length and width, and can be filled with an arbitrary amount of fluid (typically about 75 ul) which does not rise above the level of the liquid in the buffer chamber.

The procedure for device operation is as follows:
1. Construct the device by sealing the membranes between the chambers with the membrane porosity chosen to prevent crossing of stray quantum dots into the DNA solution.
2. Fill the buffer chambers with TBE electrophoresis buffer. This prevents the system from generating excessive Acid/Base at the electrodes, which can change the charge of the quantum dots or other objects to be attached to the DNA. The strength of the buffer can be modulated to change the driving force, such as rate of electroosmosis.
3. In the negative hybridization chamber is placed the DNA backbones which were created in the first part of the experiment, mixed in with 75 ul of TBE buffer.
4. In the positive chamber is placed quantum dots mixed in with 75 ul of TBE. The amount of Qdots is at least an order of magnitude higher than the calculated number of biotin binding sites present on the backbones.
5. Turn on the electric field to pull DNA backbones through the membranes. The DNA is pulled through from the negative chamber to the positive one where the quantum dots are located. The voltage should be controlled so that the rate of travel of the backbones is not too fast compared to the binding time of the biotin/streptavidin. This may include pulsing the voltage so that binding has time to occur.
6. Wait for the DNA to pull through and link through biotin-streptavidin binding to quantum dots.
7. Extract the larger chains from the solution in the positive hybridization chamber. This may involve using purification columns, or simple size exclusion using larger nanopore membranes that the quantum dots can pass but that the larger structures cannot.

Experiment 2

To create more complicated structures one needs to have a manner to bring together a large number of different objects. The procedure relies on the manufacturing of two classes of objects. The first class is mono-derivatized nanocomponents. For example, this would be a quantum dot with a single strand of DNA attached. The second class of object would be a single stranded DNA backbone. This backbone would be complementary in different sections to several different DNA sequences, which would be connected to various different structures (such as different types of quantum dots.)

One method for creating mono-derivatized quantum dots is described as follows:
1. Take the chains of quantum dots manufactured in Experiment I. These are such that the same DNA sequence repeats regularly with every quantum dot unit.
2. Mix the DNA/quantum dot chains with a restriction enzyme. A restriction enzyme cleaves DNA at a specific sequence. If the original subunits in the backbone were designed such that a restriction target was incorporated, then every quantum dot unit can be cleaved apart, each having only one DNA double stranded DNA segment on it.
3. The mixture is then heated to remove the half of the double stranded DNA which is not biotinylated to the quantum dot.
4. The mixture is then purified (by size exclusion, electrophoresis, etc) to remove dehybridized DNA in solution before it can reattach.
5. The end result is singly DNA modified quantum dots.

Form there, various singly modified quantum dots can be mixed with a backbone that can hybridize to all of them. From here, the construct can be ligated together (as in experiment 1) to create additional structural stability.

Experiment 3

The method in Experiment 2 is one way to create a set of singly modified quantum dots. Another method is as follows.
1. The chamber/membrane device would be configured to have three chambers as follows: The negative chamber would contain a solution of single stranded biotinylated DNA in buffer. The middle chamber would contain a mixture of streptavidinated quantum dots and buffer, and the positive chamber would contain only buffer. The total volume of each of the chambers being 75 ul.
2. The membranes between the outer buffer chambers and the positive and negative chambers would have 10 nm pores, as would the membrane between the negative and middle chamber. The membrane between the middle chamber and the positive chamber would have pore sizes large enough such that quantum dots an pass through under favorable conditions (~30 nm pore.)
3. When voltage is applied to the device, several effects are observed. The DNA and quantum dots, which are negatively charged, will be pulled towards the positive chamber. At that same time, electroosmotic pumping will cause liquid to move towards the negative chambers. The pumping is not sufficient to prevent the flow of DNA across the membranes, but it can prevent the flow and limit the diffusion of quantum dots which are larger and less charged.
4. One can make use of these two facts to use a window where a quantum dot that has been hybridized to a single piece of DNA now has sufficient charge to be pulled through from the middle chamber into the positive chamber against the electroosmotic flow. At the same time we intend to exploit size exclusion effects to prevent quantum dots with two DNAs attached from being able to move through the pores, since the DNA is on the same size scale as the quantum dot.

References (1) Michael Heller, Self-organizing molecular photonic structures based on chromophore- and fluorophore-containing polynucleotides and methods of their use, U.S. Pat. No. 5,532,129 Jul. 2, 1996.

(2) Nadrian C. Seeman, At the Crossroads of Chemistry, Biology, and Materials: Structural DNA Nanotechnology, Chemistry & Biology, Vol. 10, 1151-1159, December, 2003.

(3) Hao Yan, Sung Ha Park, Gleb Finkelstein, John H. Reif, Thomas H. LaBean, DNA-Templated Self-Assembly of Protein Arrays and Highly Conductive Nanowires, Science 26 Sep. 2003, Vol. 301.

(4) Hao Yan, Thomas H. LaBean, Liping Feng, and John H. Reif, Directed nucleation assembly of DNA tile complexes for barcode-patterned lattices, PNAS Jul. 8, 2003 Vol. 100 (14):8103-8108.

(5) Sarah J. Kodumal, Kedar G. Patel, Ralph Reid, Hugo G. Menzella, Mark Welch, and Daniel V. Santi, Total synthesis of long DNA sequences: Synthesis of a contiguous 32-kb polyketide synthase gene cluster, PNAS Nov. 2, 2004, Vol. 101(44):15575.

*******

The examples set forth above are provided to give those of ordinary skill in the art with a complete disclosure and description of how to make and use the preferred embodiments of the compositions, and are not intended to limit the scope of what the inventors regard as their invention. Modifications of the above-described modes for carrying out the invention that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A system for controlled fabrication of functionalized nanostructures comprising:
    a) a first chamber containing a solution of polymers derivatized with a first binding partner at regular intervals;
    b) a nanopore structure with a plurality of defined nanopores therethrough;
    c) a second chamber in fluid communication with the first chamber through the nanopore structure containing a solution of nanocomponents derivatized with a second binding partner that binds to the first binding partner, wherein the nanocomponents are prevented from passing through the nanopores; and
    d) a source of a driving force adapted for facilitating movement of the polymers in the first chamber through the nanopores into the second chamber within which the second binding partner binds to the first binding partner to form the functionalized nanostructures with the nanocomponents bound to the polymer at regular intervals.

2. The system according to claim 1, wherein the polymer is selected from the group consisting of: nucleic acids, modified polynucleotides, polysaccharides, inorganic polymers, organic polymers, proteins, and synthetic macromolecules.

3. The system according to claim 2, wherein the polymer is a nucleic acid selected from the group consisting of: deoxyribonucleic acid (DNA), ribonucleic acid (RNA) and a copolymer of DNA and RNA.

4. The system according to claim 2, wherein the polymer is a modified polynucleotide selected from the group consisting of: peptide nucleic acid (pNA), a nucleic acid containing a non-ribose sugar, and a nucleic acid containing a modified base or bases.

5. The system according to claim 2, wherein the polymer is a polysaccharide selected from the group consisting of polydextran, starch, glycogen and cellulose.

6. The system according to claim 2, wherein the polymer is an inorganic polymer selected from the group consisting of: glass fibers, carbon fibers and siloxane fibers.

7. The system according to claim 2, wherein the polymer is a protein selected from the group consisting of an enzyme, an antibody and a polypeptide.

8. The system according to claim 2, wherein the polymer is a synthetic macromolecule selected from the group consisting of: a dendrimer, a fullerene, a crown-ether, a micelle and a liposome.

9. The system according to claim 1, wherein the first binding partner and the second binding partner are complementary nucleic acids.

10. The system according to claim 1, wherein the first binding partner and the second binding partner are epitopes and antibodies, respectively.

11. The system according to claim 1, wherein the first binding partner and the second binding partner are ligands and proteins, respectively.

12. The system according to claim 1, wherein the first binding partner and the second binding partner are biotin and streptavidin, respectively.

13. The system according to claim 1, wherein the first binding partner and the second binding partner further comprise chemically reactive entities.

14. The system according to claim 1, wherein the first binding partner and the second binding partner further comprise a metal ion and a metal ligand, respectively.

15. The system according to claim 1, wherein the nanopore structure further comprises an organic porous membrane and an inorganic porous membrane.

16. The system according to claim 1, wherein the nanopore structure further comprises an organic porous membrane selected from the group consisting of: an agarose gel, a polycarbonate membrane and a polyacrylamide gel.

17. The system according to claim 1, wherein the nanopore structure further comprises an inorganic porous membrane selected from the group consisting of: glass and silicon structures.

18. A process for controlled fabrication of functionalized nanostructures in an apparatus comprising the steps of:
    a) placing a solution containing polymers derivatized with a first binding partner at regular intervals into a first chamber;
    b) placing a solution containing nanocomponents derivatized with a second binding partner that binds to the rirst binding partner into a second chamber in fluid communication with the first chamber through a nanopore structure with a plurality of defined nanopores therethrough, wherein the nanocomponents are prevented from passing through the nanopores; and
    c) subjecting the apparatus comprising the first chamber, the second chamber and the nanopore structure to a driving force that facilitates the movement of polymers in the first chamber through the nanopores into the second chamber, wherein the second binding partner binds to the first binding partner to form the functionalized nanostructures with the nanocomponents being sequentially bound to the polymer at regular intervals along the length of the polymer.

19. The process according to claim 18, wherein the driving force is selected from the group consisting of electrical, chemical and physical forces.

20. The process according to claim 18, wherein the driving force is electrical and the source of the driving force is a pair of electrodes.

21. The process according to claim 18, wherein the driving force is chemical and the source of the driving force is a chemical gradient.

22. The process according to claim 18, wherein the driving force is physical and the source of the driving force is selected from the group consisting of: a pump, a thermostat and a vacuum.

23. The process according to claim 18 further comprising a catalyst attached at or near the nanopores.

24. A plurality of functionalized nanostructures comprising at least two different nanocomponents sequentially attached to a polymer at regular intervals in a predetermined pattern and order.

25. The functionalized nanostructures according to claim 24, wherein the nanocomponents are selected from the group consisting of: quantum dots, metallic nanoparticles, semiconductor nanoparticles, polymeric nanoparticles, carbon nanotubes, nanorods and nano wires.

26. The functionalized nanostructures according to claim 24 further comprising a sheathing particle attached to the functionalized nanostructures.

27. The functionalized nanostructures according to claim 26, wherein the sheathing particle is selected from the group consisting of: organic polymer nanoparticles, metallic nanoparticles and refractive index influencing nanoparticles.

28. The functionalized nanostructures according to claim 24 further comprising cleavage sites at predetermined intervals along the polymer.

29. The functionalized nanostructures according to claim 28, wherein the polymer further comprises nucleic acid and the cleavage sites further comprise endonuclease cleavage sites.

30. A method for controlled fabrication of functionalized nanostructures comprising the steps of: a) providing a solution of polymers derivatized with a first binding partner at regular intervals in a first chamber; b) providing a solution of nanocomponents derivatized with a second binding partner that binds to the first binding partner in a second chamber; c) contacting the polymers with the nanocomponents through a nanopore structure having a plurality of controlled permeability nanopores separating the first chamber and the second chamber, wherein the nanocomponents attach to the polymers in a predetermined pattern and order.

* * * * *